(12) United States Patent
Xiaofeng Nie

(10) Patent No.: US 12,053,431 B2
(45) Date of Patent: Aug. 6, 2024

(54) AUTOMATIC ACUPUNCTURE ROBOT

(71) Applicant: Oriental Power Inc., Richmond Hill (CA)

(72) Inventor: Eileen Xiaofeng Nie, Richmond Hill (CA)

( * ) Notice: Subject to any disclaimer, the term of this patent is extended or adjusted under 35 U.S.C. 154(b) by 187 days.

(21) Appl. No.: 17/891,292

(22) Filed: Aug. 19, 2022

(65) Prior Publication Data

US 2024/0058210 A1 Feb. 22, 2024

(51) Int. Cl.
| | |
|---|---|
| *A61H 39/02* | (2006.01) |
| *A61B 5/00* | (2006.01) |
| *A61B 5/055* | (2006.01) |
| *A61H 39/00* | (2006.01) |
| *A61H 39/06* | (2006.01) |
| *A61H 39/08* | (2006.01) |
| *B25J 9/16* | (2006.01) |
| *B25J 15/00* | (2006.01) |

(52) U.S. Cl.
CPC ........... *A61H 39/02* (2013.01); *A61B 5/0036* (2018.08); *A61B 5/0042* (2013.01); *A61B 5/055* (2013.01); *A61H 39/002* (2013.01); *A61H 39/007* (2013.01); *A61H 39/06* (2013.01); *A61H 39/086* (2013.01); *B25J 9/1633* (2013.01); *B25J 15/0028* (2013.01); *A61H 2201/1607* (2013.01); *A61H 2201/1659* (2013.01); *A61H 2201/5061* (2013.01)

(58) Field of Classification Search
None
See application file for complete search history.

(56) References Cited

U.S. PATENT DOCUMENTS

| | | | |
|---|---|---|---|
| 2019/0053760 A1* | 2/2019 | Gerald, II | ............ G01R 33/286 |
| 2020/0126297 A1* | 4/2020 | Tian | ...................... G06T 7/0012 |
| 2021/0046315 A1* | 2/2021 | Popescu | ............. A61N 1/36071 |

(Continued)

FOREIGN PATENT DOCUMENTS

| | | | | |
|---|---|---|---|---|
| CN | 102846466 A | * | 1/2013 | |
| CN | 104644434 A | * | 5/2015 | ........... A61H 39/086 |
| CN | 106003054 A | * | 10/2016 | ............ B25J 9/0009 |

(Continued)

OTHER PUBLICATIONS

Lan et al., "Robot-Controlled Acupuncture—An Innovative Step towards Modernization of the Ancient Traditional Medical Treatment Method," (Aug. 10, 2019), Medicines 2019, 6, 87. (Year: 2019).*

(Continued)

*Primary Examiner* — Joel Lamprecht
*Assistant Examiner* — Ashish S Jasani
(74) *Attorney, Agent, or Firm* — Nasser Ashgriz; UIPatent Inc.

(57) ABSTRACT

A medical apparatus for performing electroacupuncture for treatment of traumatic brain injury and cerebral thrombosis is disclosed. The device comprising a 6-DOF (Degree of freedom) Robotic arm, a multi-functional tool tip, an acupuncture friendly MRI helmet and a Magnetic resonance imaging (MRI). The Acupuncture Robot is able to operate with certain needles automatically by inserting a needle, turning, or shaking in certain frequency ranges and apply electrical stimulation to enhance the effects.

8 Claims, 16 Drawing Sheets

(56) References Cited

U.S. PATENT DOCUMENTS

2022/0031565 A1* 2/2022 Yim ............... A61H 39/002
2022/0336080 A1* 10/2022 Monteverde ............ G06T 7/70

FOREIGN PATENT DOCUMENTS

| CN | 108392412 B | * | 9/2019 | ............ A61H 39/08 |
| CN | 111494202 B | * | 3/2024 | ............ A61H 39/02 |

OTHER PUBLICATIONS

Zhang et al., "A Visual Servo Controlled Robotic System for MRI-guided Breast Biopsy," (Aug. 2, 2022), Journal of Intelligent & Robotic Systems (2022) 105: 86. (Year: 2022).*

Xu et al., "Guidance for Acupuncture Robot with Potentially Utilizing Medical Robotic Technologies," (Mar. 31, 2021), Evidence-Based Complementary and Alternative Medicine, vol. 2021. (Year: 2021).*

* cited by examiner

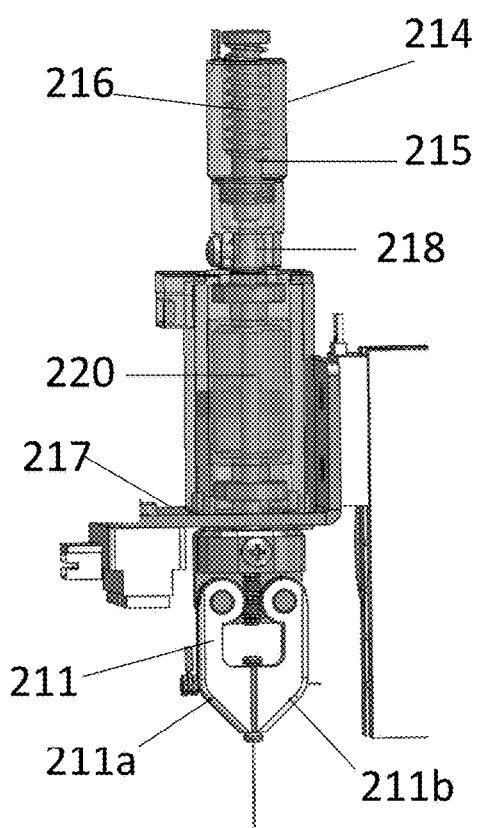
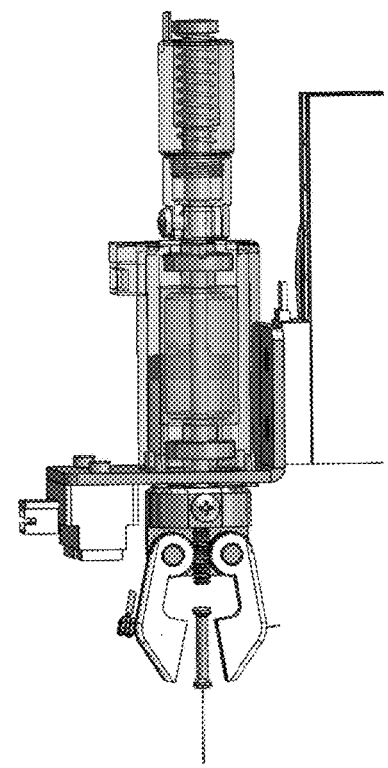
FIG. 9A                    FIG. 9B

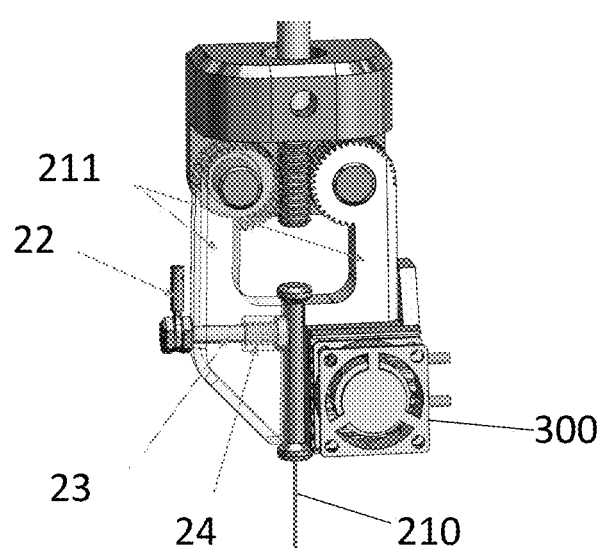
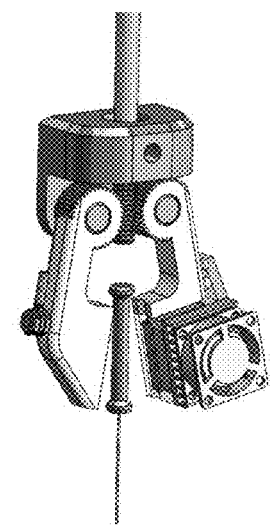
FIG. 10A
FIG. 10B

AUTOMATIC ACUPUNCTURE ROBOT

FIELD OF THE INVENTION

The present invention relates in general to the field of medical devices and in specific to an automatic acupuncture device.

BACKGROUND OF THE INVENTION

Acupuncture originated in China approximately 2000 years ago and is one of the oldest medical procedures in the world. The ancient art of acupuncture have been used in Asia for centuries to treat many conditions and relief pain. It's now being used in the United States and other countries to heal diseases from low back pain to nerve pain and headaches, fibromyalgia, menstrual cramps, etc. Traditional Chinese acupuncture involves the insertion of very fine needles (Ø0.25-0.35 mm) into the skin at specific "acupoints of the meridians." This acupuncture may relief pain by the body secreting endorphins, the body's natural pain-killing chemicals, and by affecting the part of the brain that governs serotonin, a brain chemical involved within Chinese acupuncture, the acupuncturist may turn or twirl the needles slightly or apply electrical stimulation to enhance the effects.

Acupuncture works by increasing the circulation of blood, relaxing muscles, and stimulating the production of neurotransmitters like endorphins and serotonin, which will result in relaxation and pain relief. Acupuncture can cause multiple biological responses, including circulatory and biochemical effects. These responses can occur locally or close to the site of application, or at a distance. They are mediated mainly by sensory neurons to many structures within the central nervous system. This can lead to activation of pathways affecting various physiological systems in the brain as well as in the periphery.

Recent research suggests that acupoints may be excitable muscle/skin-nerve complexes containing a high density of nerve endings. Needles can produce a wide range of neural effects in the spinal cord, brain stem, limbic system, hypothalamus and cortex. Needles can alter perception, autonomic activity and immune responses.

Electroacupuncture is one of the modern acupunctures. It is applied by micro-electricity to stimulate patients' bodies inducing more therapeutic effects. The electroacupuncture method is like Chinese Traditional Acupuncture. The needles are placed in the same spots of the meridians, in which the small electrodes are attached to the needles. A micro-electricity (from 1 mA-3 Am of current) runs through the electrode with a little vibration (1-50 Hertz) or soft hum during treatment. The treatments are also shorter because the electrodes can activate acupuncture points more quickly, furthermore the electrode needles in the body's with conductive micro-electricity will result in repairing power to the bodies.

SUMMARY OF THE INVENTION

The present invention is an electroacupuncture device comprising a 6-DOF (Degree of freedom) Robotic arm, a multi-functional tool tip, and a Magnetic resonance imaging (MRI). The tool tip has a needle with vibration mechanism. The Acupuncture Robot is able to operate acupuncture automatically with certain needles by inserting a needle, turning, or shaking in certain frequency ranges and apply electrical stimulation to enhance the effects. The Chinese Traditional Acupuncture and electroacupuncture have demonstrated the efficacy of stopping pain and improving balance function, reducing spasticity, and increasing muscle strength and general well-being post-stroke, etc.

In one embodiment as depicted in this application the robot module is primarily designed for the treatment of traumatic brain injury and cerebral thrombosis, but it also can be used for other medical applications. In this application the electroacupuncture device has an acupuncture MRI helmet having a coil inside which is necessary for MRI. When a radiofrequency is transmitted into a patient body, the coil acts as an antenna to receive the radio frequency signal coming out of the body and transmit that data to a computer which then generates images. The helmet can show most of the acupoints for the acupuncture robot.

The MRI of the device produces detailed pictures of the brain and other cranial structures that are clearer and more detailed than other imaging methods. In this way, the occupant can find the locations and the shapes of the cerebral thrombosis, then gives an acupuncture prescription. The robot also needs these MRI images to locate the acupoints.

The robot could be driven by a servo motor moving along two curved guides to different locations. A linear motor is added to drive a griper of the needle up and down. With this linear motor, the needle could quickly and smoothly stick in and out of the human body with accurate depth.

The device further has a heating or cooling module. A Peltier cooler/heater or thermoelectric heat pump which is a solid-state active heat pump, transfers heat from one side of the device to the other side, with the consumption of electrical energy, depending on the direction of the current. This can be used either for heating or for cooling.

For the accuracy and safety reason, an ultrasonic distance sensor is used for determining the distance of the needle from the target point. The ultrasonic sensor emits high-frequency sound waves towards the target object. Target object reflects the sound waves back towards the sensor. The receiver picks up the reflected wave and stops the timer. The time taken for the wave's return is calculated against the speed of sound to determine the distance travelled. This sensor has a measurement range of 1 cm-400 cm.

The device further has a force sensor in order to control the operation precisely and to measure the needle inserting force. If the resistance to the needle is bigger than the setting limit, the linear motor will stop rapidly.

In operation a patient lays down on the treatment table and the head is placed inside the MRI helmet. The MRI will work to scan the patient's head. After scanning, the MRI will get the 3D information of the head and find the cerebral thrombosis (or pathologic processing changes such as cerebral edema). An acupuncturist or an AI software will give an acupuncture prescription according to certain information provided by the images of the MRI scan test. Then the robot locates the acupuncture points and performs treatment according to the acupuncture prescription.

It is therefore an object of the present invention to provide an electro acupuncture device that can improve and enhance the treatment effect of traditional acupunctures.

It is another object of the present invention to increases the physiologic capacity of the acupuncture and well fit by the control of various electrical stimulation in ultra-precision.

It is another object of the present invention that can perform the most of human acupuncture techniques on human brains and bodies; with more efficiency and reduce human errors.

It is another object of the present invention that can be used for the acupuncture prescriptions, especially the acupuncture prescriptions for traumatic brain injury and cerebral thrombosis.

It is another object of the present invention that can automatically identify the location for all of 361 acupuncture points.

BRIEF DESCRIPTION OF THE DRAWINGS

Embodiments herein will hereinafter be described in conjunction with the appended drawings provided to illustrate and not to limit the scope of the claims, wherein like designations denote like elements, and in which:

FIG. 9A is a perspective front view of the Robot Tool Tip showing the Tip in clamp position;

FIG. 9B is a perspective front view of the Robot Tool Tip showing the Tip in released position;

FIG. 10A is a perspective front view of the gripper, according to the present invention;

FIG. 10B is a perspective front view of the gripper, according to the present invention;

DETAILED DESCRIPTION OF PREFERRED EMBODIMENTS

Figure 1A:
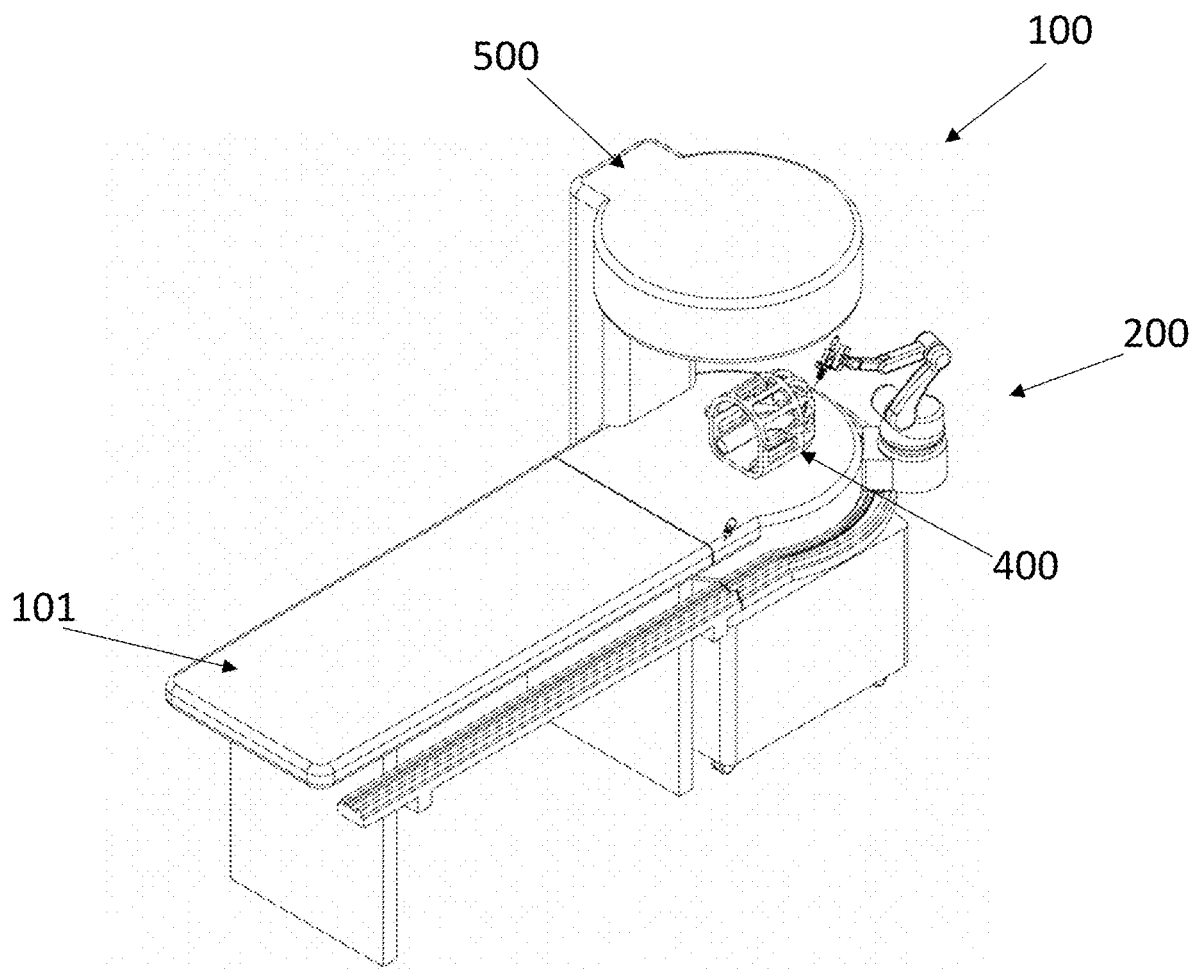
FIG. 1A is a perspective view of the electroacupuncture device according to an embodiment of the present invention.
Figure 1B:
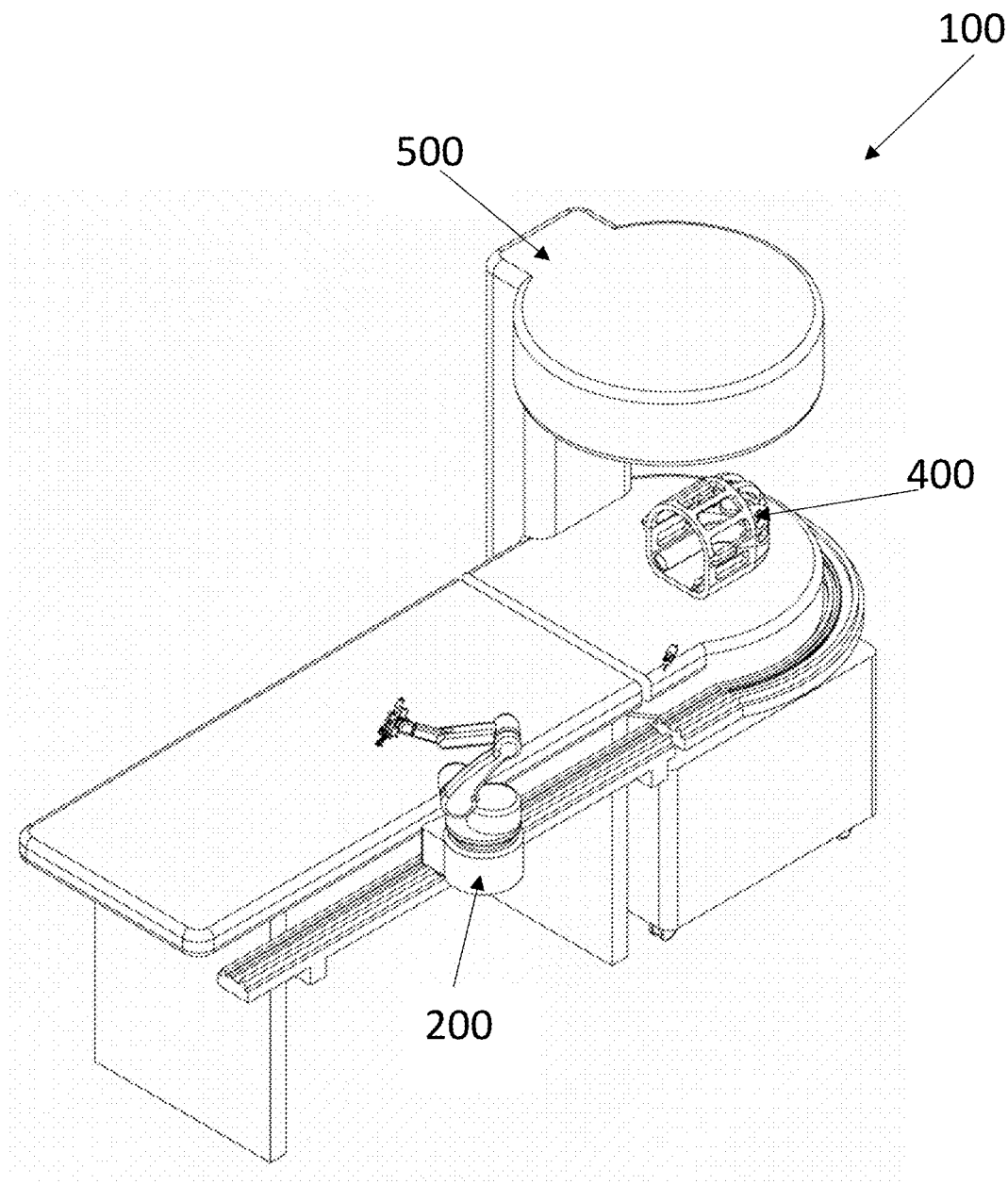
FIG. 1B is a perspective view of the electroacupuncture device according to another embodiment of the present invention
Figure 2:
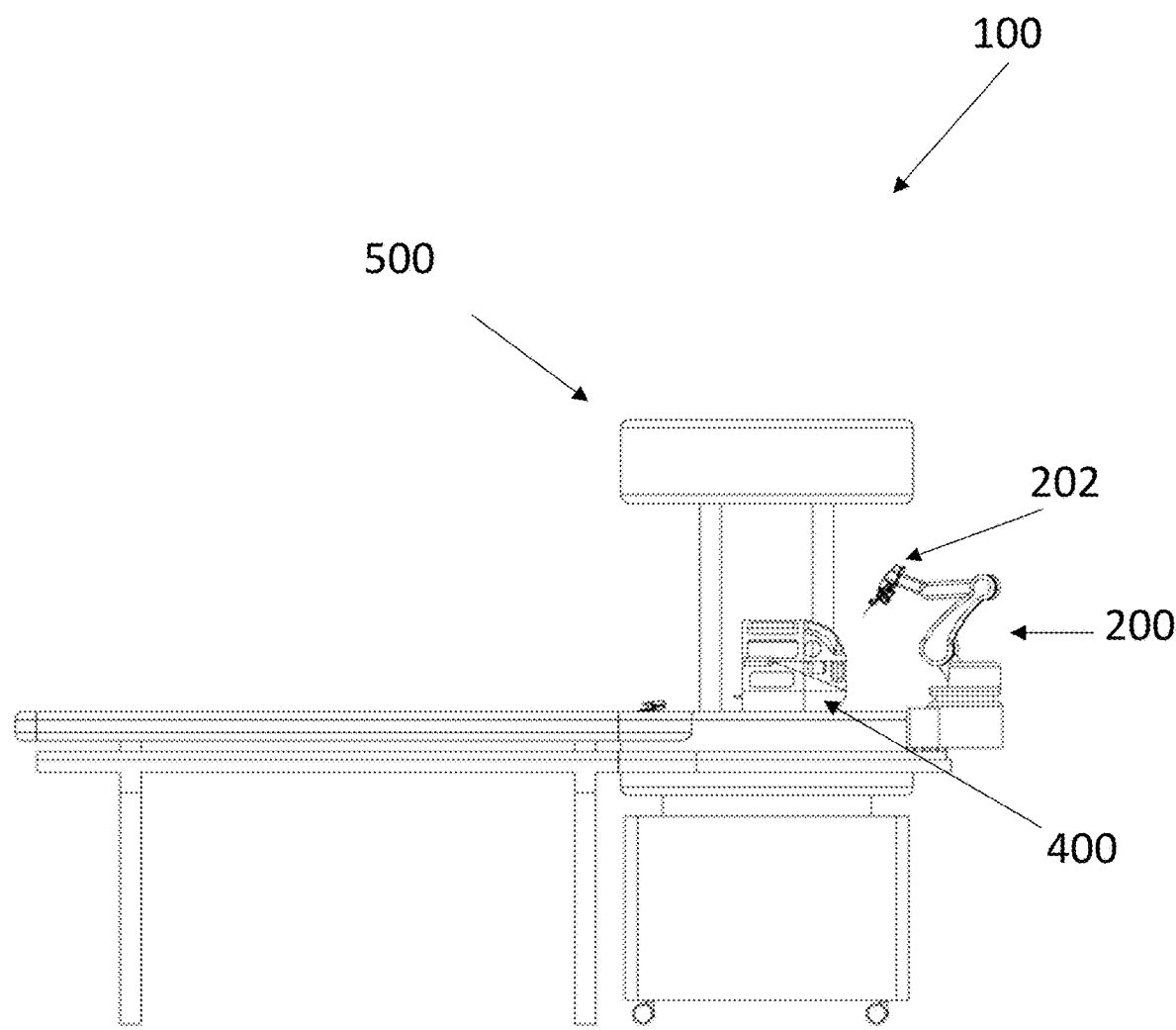
FIG. 2 is a side view of the electroacupuncture device according to an embodiment of the present invention.

FIG. 1A to 4 show the acupuncture device 100 of the present invention. The device comprising a Robotic arm 200 movable in one or more dimensions, a Magnetic resonance imaging (MRI) 500 and an acupuncture MRI helmet 400. The robot arm 200 is a 6-DOF Robotic arm and can perform most of human acupuncture techniques on human brains and bodies more efficiency and reduce human errors. An acupuncture needle 210 is coupled to the robotic arm. The robotic arm is movable so as to position the needle with respect to a target area. The MRI 500 can be detached from the bed 101. When the robot 200 moves to the bed side, the MRI 500 can automatically move away.

The Robotic arm 200 is able to automatically operate the acupuncture process with certain needles. It operates by inserting a needle 210, turning or shaking it at certain frequency ranges and apply electrical stimulation to enhance the effects. The acupuncture device 100 comprises of a bed 101 for the patient to lay thereon during the process, on which an acupuncture helmet 400 is installed on.

Figure 3:
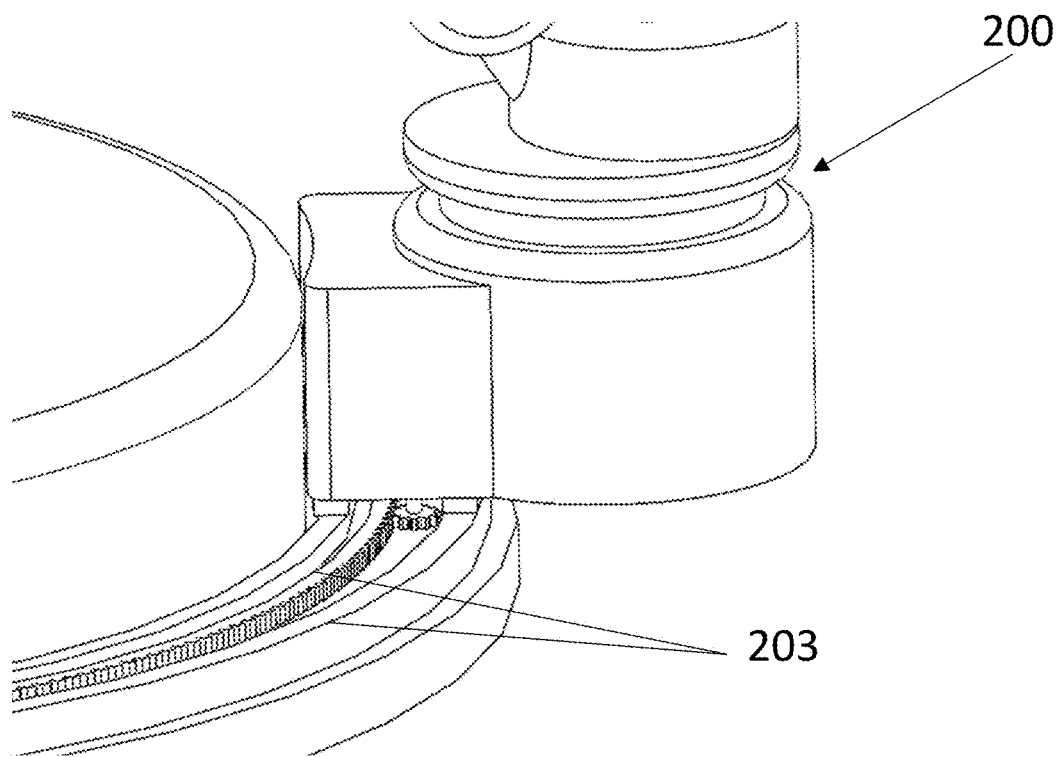
FIG. 3 is a close-up view of the Robot arm of the present invention.

The Robotic arm 200 is a 6 degrees of freedom (DOF) arm having a multi-functional tool tip 202. The robot arm 200 is driven by a servo motor 212 to various locations. As shown in FIG. 3 the movement of the robot arm 200 is along two curved guides 203.

Figure 4:
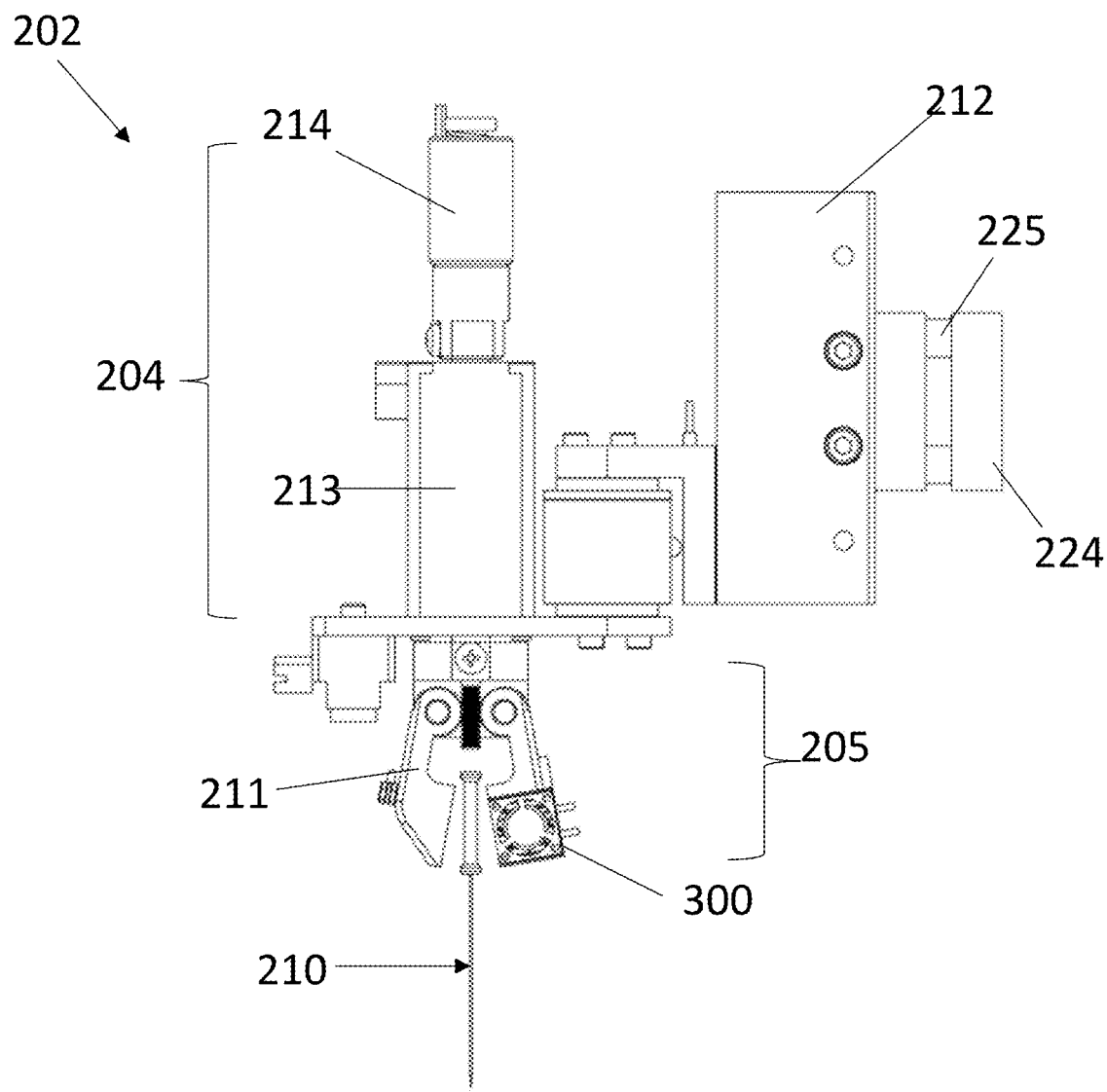
FIG. 4 is a front view showing the Robot Tool Tip Components according to the present invention.
Figure 5:
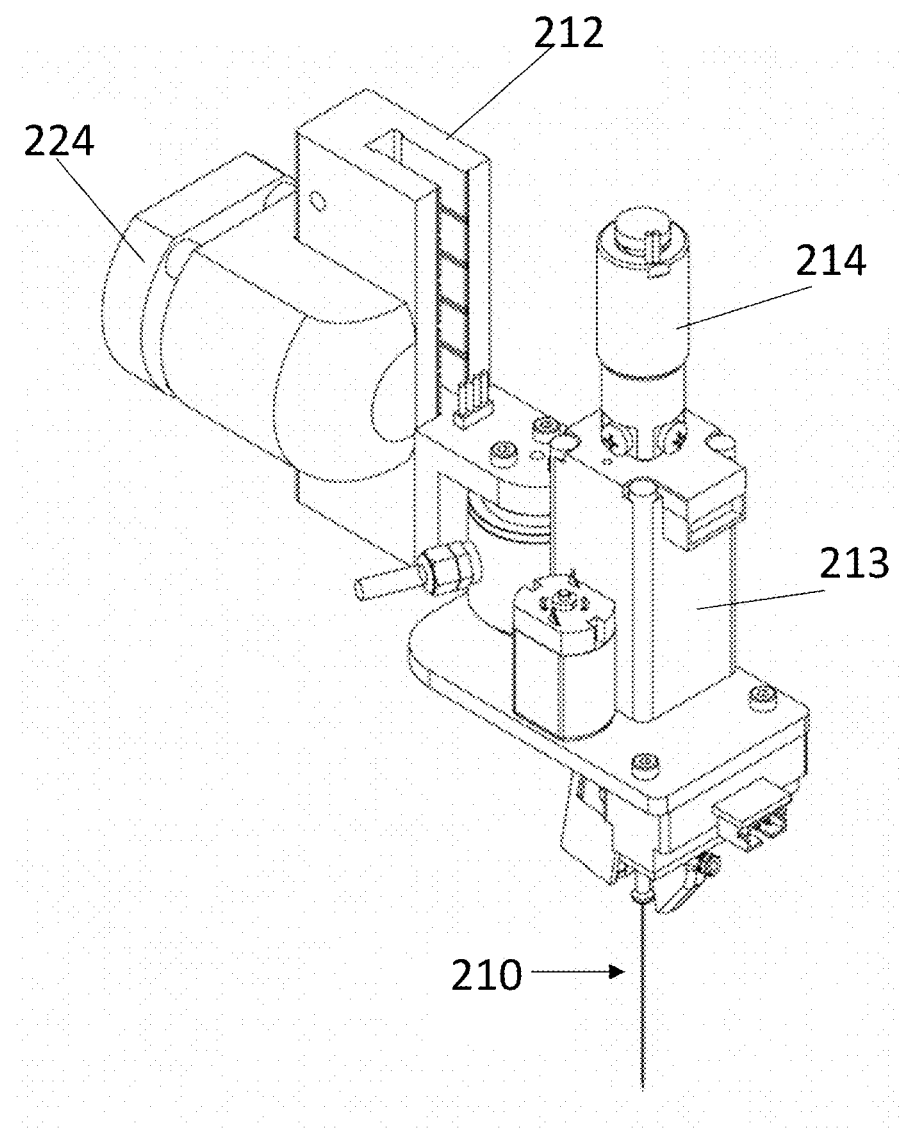
FIG. 5 is a perspective top view showing the Robot Tool Tip Components according to the present invention.
Figure 6:
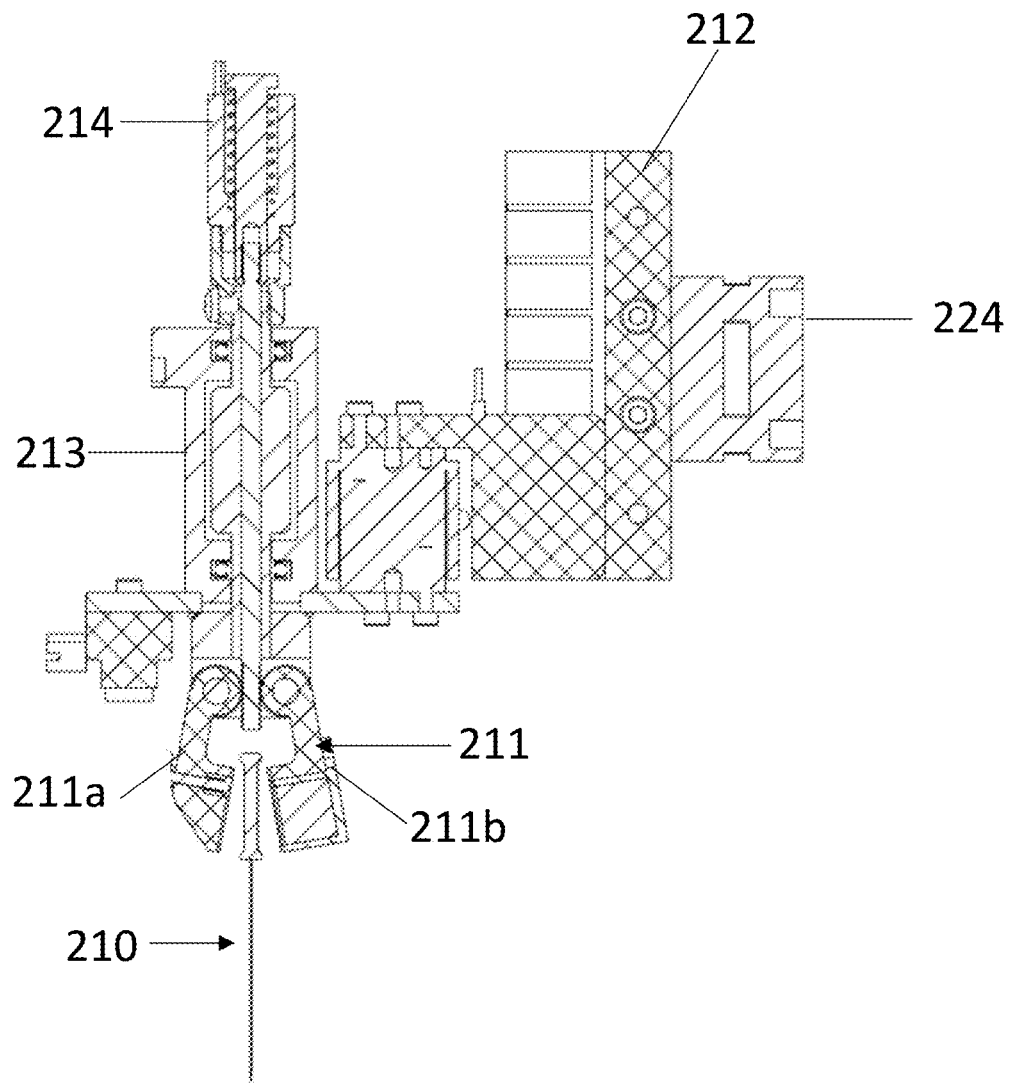
FIG. 6 is a cross-sectional view of the Robot Tool Tip showing the gripper in open position according to the present invention.

According to FIGS. 4, 5 and 6, the tool tip 202 has an upper portion 204 and a lower portion 205. The lower portion of the tool tip 205 comprises a needle 210 with a gripper 211 that includes a translation and rotational mechanism operably coupled to the robotic arm 200 and arranged so that the needle moves and inserts into the tissue. The gripper 211 holds and grips the needle 210. The Tool Tip has a mechanism that can turn or twist the needle. A linear motor 212 is added to drive griper 211 up and down. With this linear motor 212, the needle 210 can quickly and smoothly penetrate in and out of the human body with an accurate depth. A hollow shaft motor 213 is provided to turn the gripper 211 ±180 degrees. A solenoid 214 can be turned ON/OFF to Open/Close the gripper fingers 211a and 211b. Such a translation and rotational mechanism includes a pivoting structure and a rotational structure to the robot arm 200. The pivoting structure is configured so as to cause the needle 210 to move along an axis of the device. The insertion of the needle 210 is nearly linear and is guided by the linear motor 212. A parallel motion mechanism is provided to maintain the direction of the needle during insertion. The robotic arm 200 includes a mechanism that causes the needle 210 to rotate about the long axis of the needle.

The needle 210 further has a vibration mechanism. A vibration motor 224 causes the vibration of the needle 210. When vibration motor 224 is on, 4 rubber isolators 225 isolate the oscillatory wave to the left side of the tool tip 202; meanwhile, the right side of the tool tip gets stronger vibration.

Figure 7:
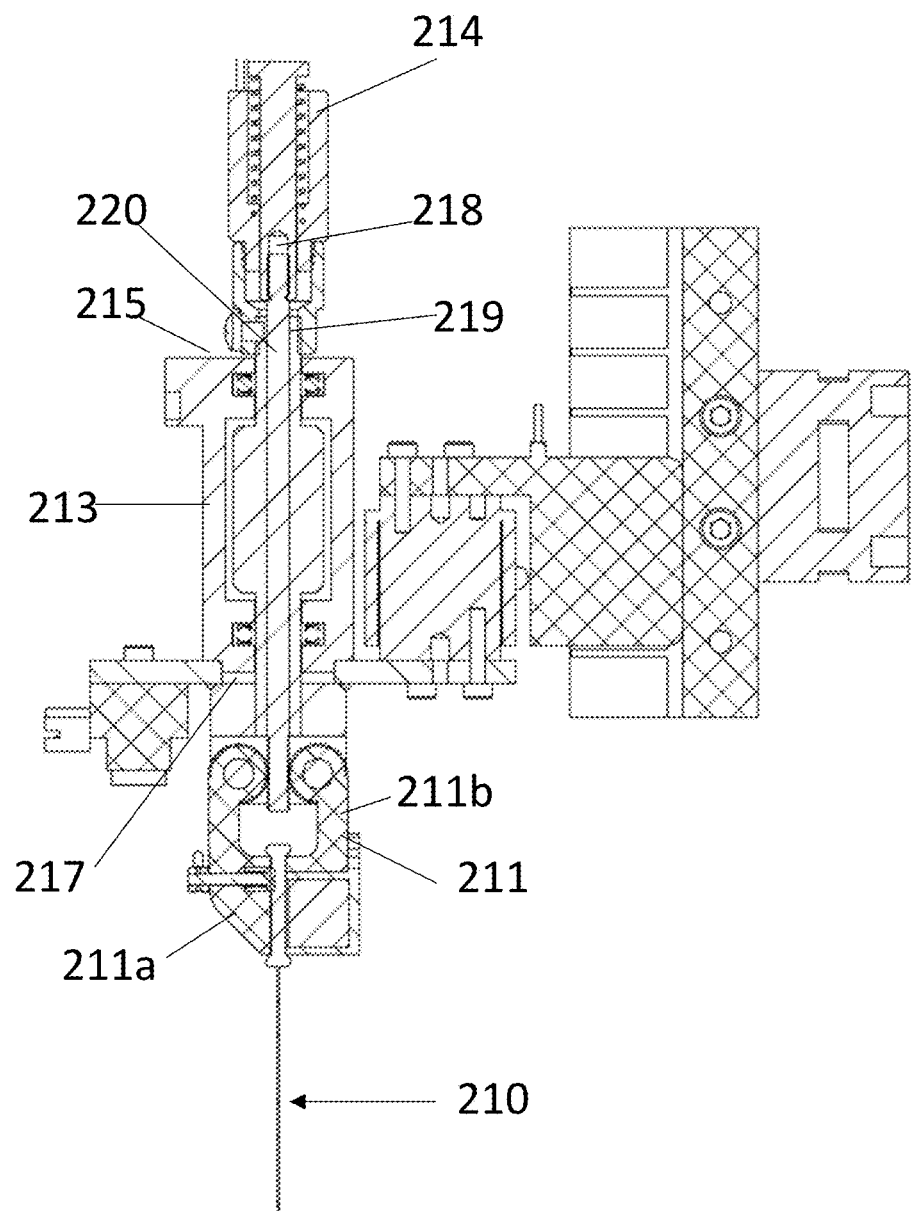
FIG. 7 is a cross-sectional view of the Robot Tool Tip showing the gripper in closed position according to the present invention.
Figure 8:
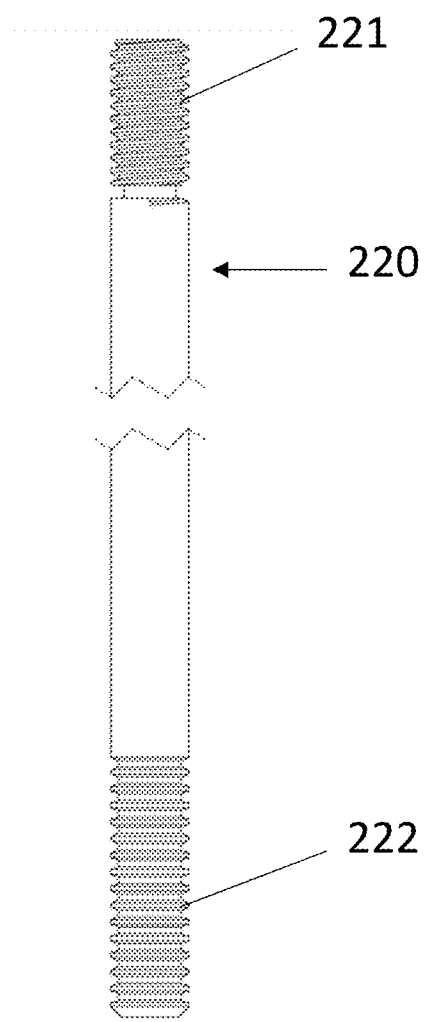
FIG. 8 shows the gripper long pin of the present invention.

Referring to FIGS. 7 and 8, the device 100 has a Gripper Long Pin 220 that is made of stainless steel. The top side of pin 221 is threaded to connect with a solenoid pin 218; the bottom side of the pin 222 is rack teeth to drive gripper fingers 211a, 211b. The gripper 211 is fixed on the bottom of the shaft motor 217. When the solenoid 214 is OFF, a solenoid spring pulls the gripper long pin 220 up, then the gripper fingers 211a, 211b are pulled to clamp the needle 210 securely. When the solenoid 214 is ON, a solenoid plunger will push the gripper long pin 220 down to release the needle 210. Connectors 219 fix the solenoid 214 on motor shaft top 215. One of the main differences between the present device and the previous devices used for acupuncture is that the driver is usually taller than the needle which limits the applications. The device 100 of the present invention is configured to achieve a linear motion.

Referring now to FIGS. 9A to 10B, the lower part 205 of the tool tip is shown in closed and opened position. FIGS.

9A and 10A show the gripper 211 in a closed position and in an open position, respectively. The tool tip 202 includes a gripper 211, which provides a mechanism for releasing the needle 210 quickly, automatically, and very smoothly, without moving or pushing it while also securing the needle for insertion. FIG. 9A shows the position of the gripper 211 when the solenoid 214 is OFF. In this position, the solenoid spring 216 pulls the gripper long pin 220 up, then the gripper fingers 211a, 211b are pulled to clamp the needle 210 securely.

FIG. 9B shows the gripper 211 position when the solenoid 214 is ON. When the solenoid 214 is ON, the solenoid plunger pushes the gripper long pin 220 down to release the needle 220. Connectors 218 fix solenoid 216 on motor shaft top 217.

The needle 210 is held in the gripper 211 by the gripper fingers 211a, 211b in close proximity of the skin. The needle 210 is configured to be operably coupled to rotational and translational structure so as to spin and insert in the tissue while the gripper 211 guides the needle's 210 direction. The spinning translating needle resulting from the translating, rotating movement causes the needle 210 to spiral in, rather than deflecting on a side. This allows the needle 210 to be placed closer to the target. Such spinning translating needle movement also breaks the static friction between the tissue and the target, thereby reducing forces and further possibly reducing insertion forces.

The gripper mechanism of the present invention holds the needle by its head and provides an additional needle support guide for the gripper part which is located in close proximity of the skin entry point. This is similar to holding a needle with two hands, one from its head and one from its barrel next to the skin, where one hand pushes the needle in and out, and the lower holds the guide to support the direction of the needle as close as possible to the skin. This mechanism is configured to release the needle 210 quickly, automatically, and very smoothly, without moving or pushing on the needle. The process of mounting the needle 210 is accomplished manually.

As shown in FIG. 10A, the gripper 211 may have a one-piece construction made of a material appropriate for the intended use. In an illustrative embodiment, the grippers are made of UPE material. The needle 210 is constructed of materials that are appropriate for the intended use such as, for example, metal (stainless steel) for the needle and plastic for the other functionalities.

Figure 11A:
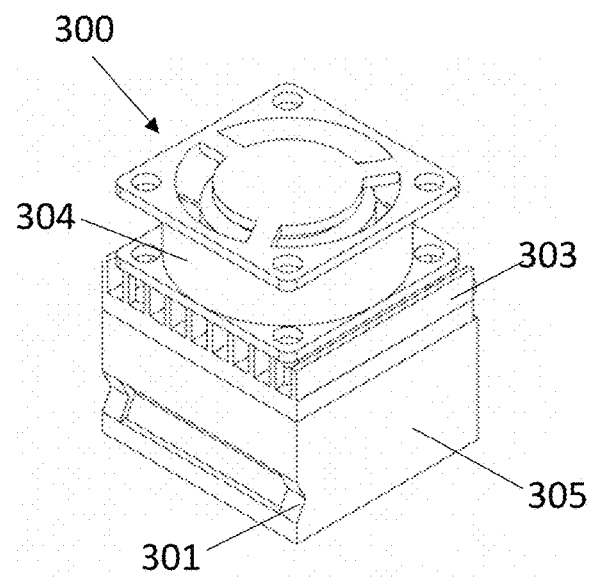
FIG. 11A is a perspective view of the needle heating and cooling system of the present invention.
Figure 11B:
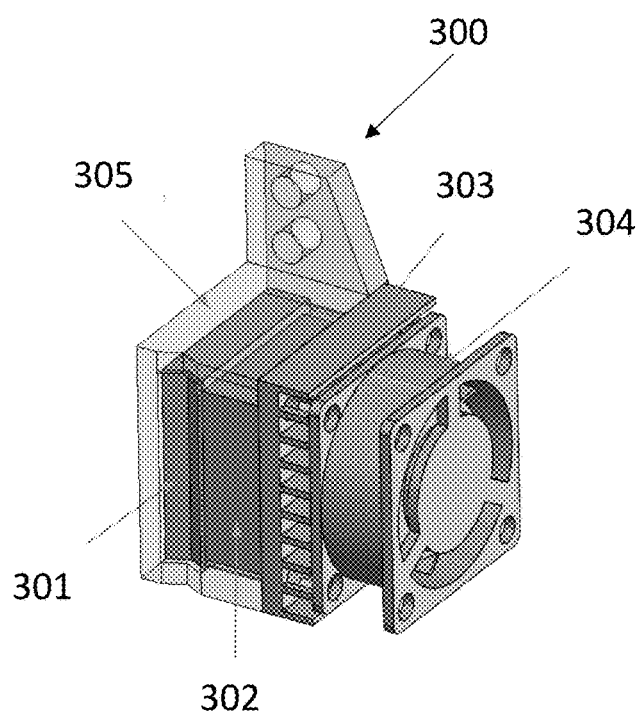
FIG. 11B is a perspective side view of the needle heating and cooling system of the present invention.

According to FIG. 4, the device 100 provides a heating and cooling module 300 for heating or cooling acupuncture treatment. In one embodiment, as in FIGS. 11A and 11B, a Peltier cooler/heater or thermoelectric heat pump (a solid-state active heat pump) is used that transfers heat from one side of the device to the other. Depending on the direction of the current, these devices can be used either for heating or for cooling. In the present design, the Peltier can control the work pad 301 temperature from 1° C. to 60° C. for the cold or hot acupuncture treatment. The Heating and cooling module 300 has a Peltier cooler/heater 302, a heat sink 303, a fan 304 and an isolation case 305. The heating and cooling module 300 is placed on the gripper 211 to heat or cool the acupuncture needle 210.

According to FIGS. 10A again and 12 in one embodiment the device has a positive electrode 22 on a metal pin 23 to touch the needles 210, and the negative electrode is on the finger clip 25. The voltage is 3 V, and the current could be adjusted from 0-10 mA output range with 0.1 mA increments.

This device 100 is primarily designed for the treatment of traumatic brain injury and cerebral thrombosis, but it also can be used for other medical applications. In this application the device has a MRI helmet 400. The MRI 500 uses a powerful magnetic field, radio waves and a computer to produce detailed pictures of the brain and other cranial structures that are clearer and more detailed than other imaging methods. In this way, the doctor can find the locations and the shapes of the cerebral thrombosis, then give an acupuncture prescription. The robotic arm 200 also needs these MRI images to locate the acupoints.

Figure 12:
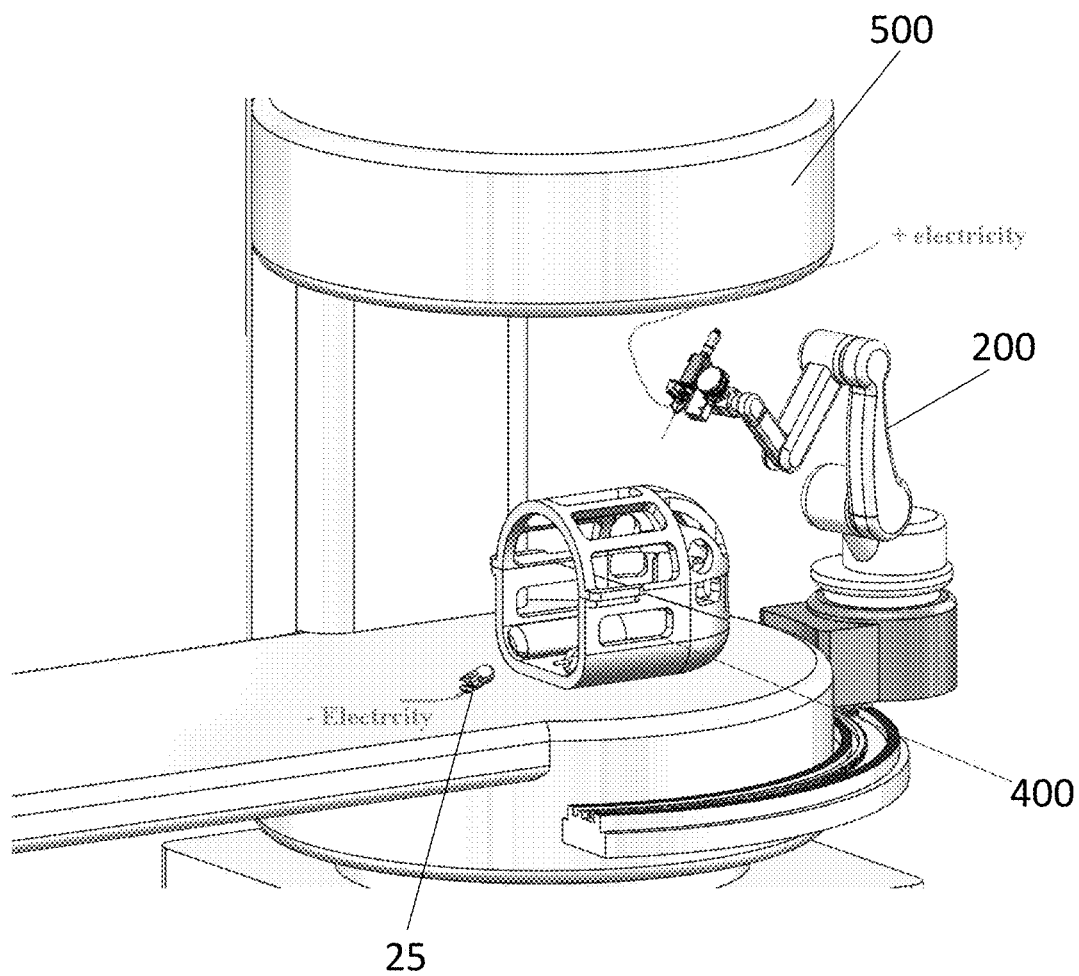
FIG. 12 is a perspective view of the electroacupuncture device showing the relation of the components according to the present invention.
Figure 13:
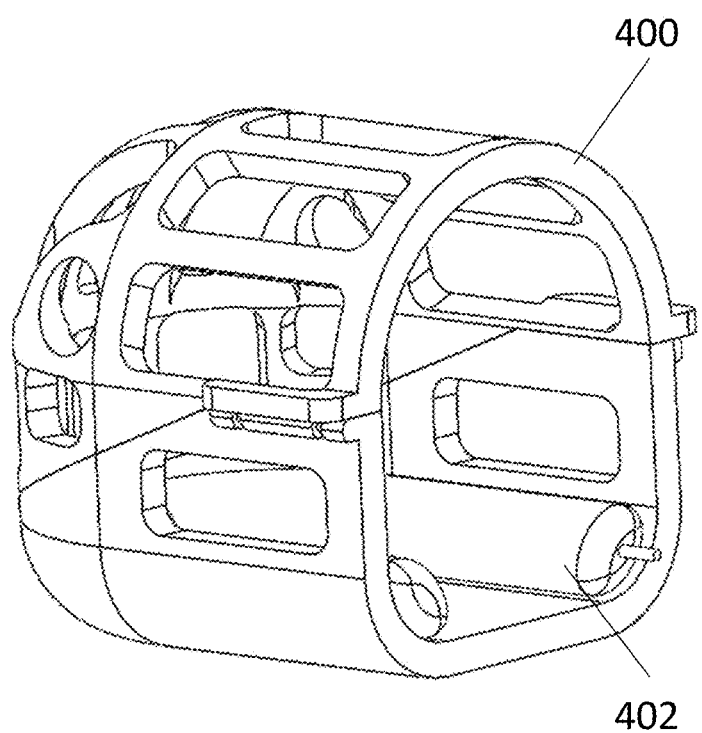
FIG. 13 is a perspective view of the acupuncture helmet according to the present invention.

As shown in FIGS. 12 and 13, helmet 400 has a coil inside which is necessary for MRI. When a radiofrequency is transmitted into a patient body, the coil acts as an antenna to receive the radio frequency signal coming out of the body and transmit that data to a computer which then generates images. The helmet 400 can show most of the acupoints for the acupuncture robot. Inside the helmet, there is an airbag 402 that can be inflated or deflated to fit the different size heads.

Figure 14A:
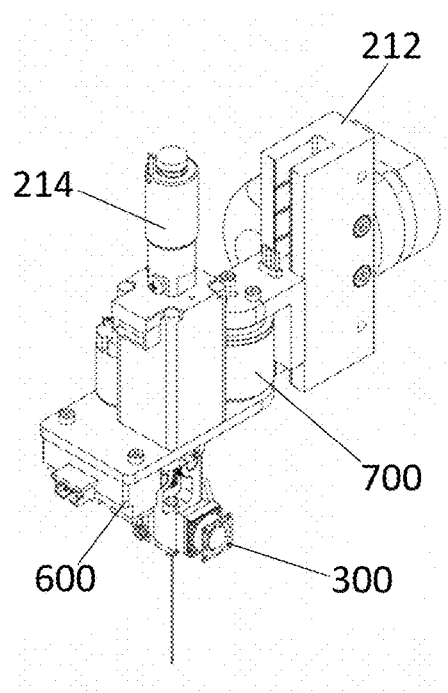
FIG. 14A is a perspective front view of the Robot Tool Tip of present invention.
Figure 14B:
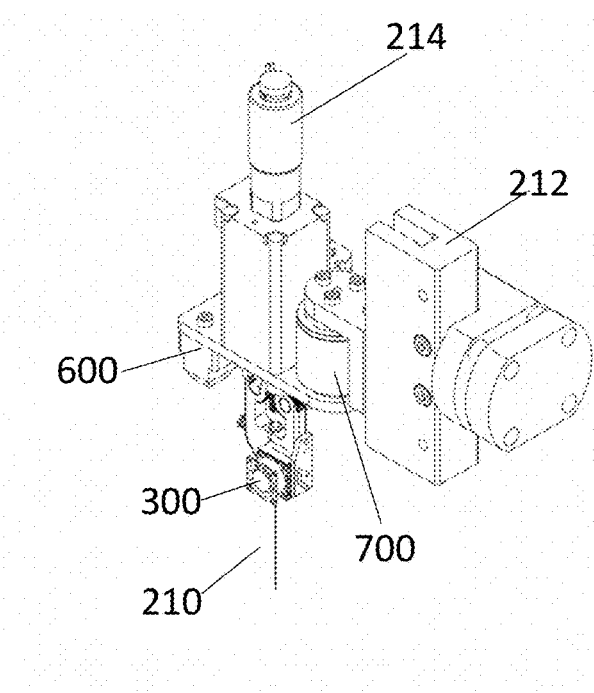
FIG. 14B is a perspective back view of the Robot Tool Tip of the present invention.
Figure 15:
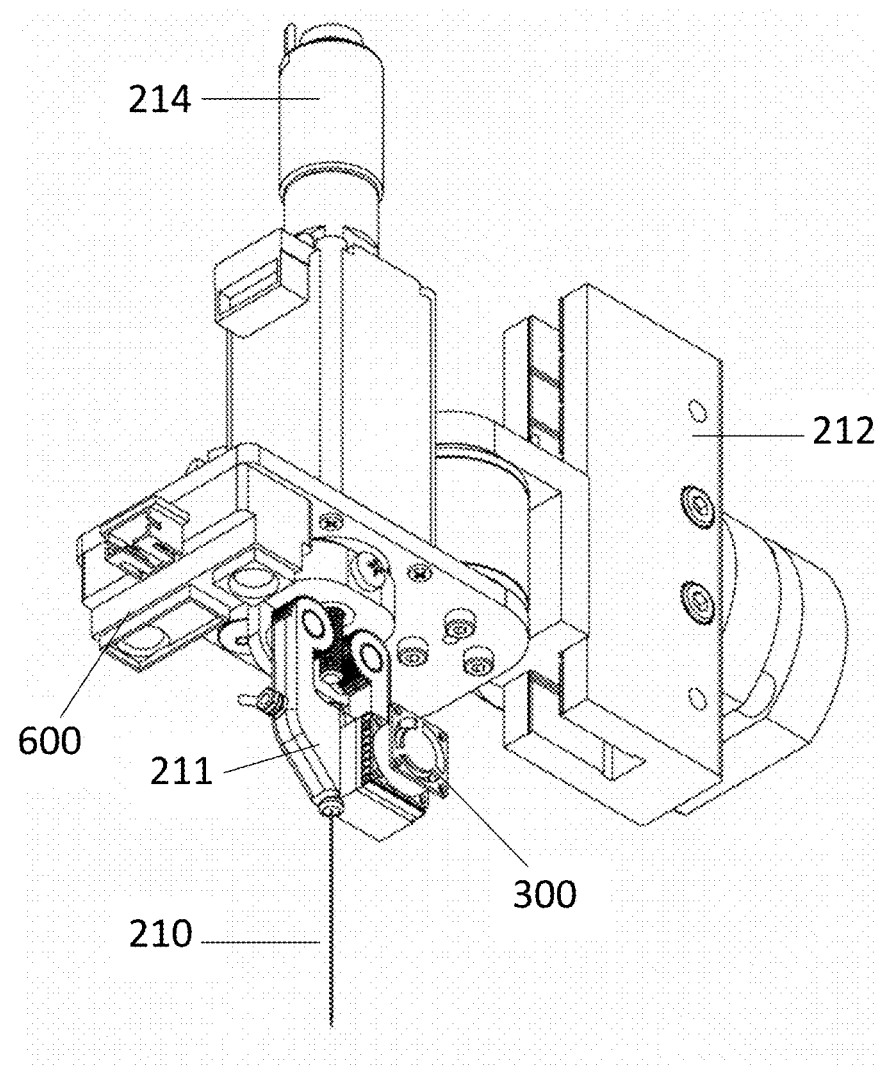
FIG. 15 is a perspective bottom view of the Robot Tool Tip of the present invention.

According to FIGS. 14A, 14B and 15 for the accuracy and safety reason, an ultrasonic distance sensor 600 is used for determining the distance of the needle 210 from the acupoints on human head. The ultrasonic sensor 600 emits high-frequency sound waves towards the target object, and a timer is started. Target object reflects the sound waves back towards the sensor 600. The receiver picks up the reflected wave and stops the timer. The time taken for the wave's return is calculated against the speed of sound to determine the distance travelled. This sensor 600 has a measurement range of 1 cm-400 cm.

The present device further has a force sensor 700 in order to control the operation precisely and to measure the needle inserting force. If the resistance to the needle 210 is bigger than setting limit, the linear motor 212 will stop rapidly.

Referring to FIGS. 1, 2 and 12 again in operation after a patient is laid down on the treatment table 101 with his/her head covered inside the MRI helmet 400; the MRI 500 scans the patient's head. After scanning, the MRI 500 will get the 3D information of the head and finds the cerebral thrombosis (or pathologic processing changes such as cerebral edema). An acupuncturist or an AI software will give an acupuncture prescription according to certain information provided by the images of the MRI scan test. Then the robot 200 locates the acupuncture points and performs treatments according to the acupuncture prescription.

The Robot arm 200 cleans the local skin around acupuncture-points with 75% Alcohol as a disinfectant. Then the needle 210 is placed at the desired skin entry point, so that before inserting the needle 210 the orientation of the needle is adjusted towards the desired target by the Robot arm 200 over the table. The mechanism of the device 100 embodies for translating and rotating the needle for purpose of inserting the needle into the tissue of a patient.

Then the needle 210 is inserted into the tissue with turning or shaking in certain frequency ranges. A physical treatment is further provided by heating or cooling from 0-65° C., from 0-60 seconds, up to 30 minutes. This increases the physiologic capacity of the acupuncture and well fits by the control of various electrical stimulation in ultra-precision. The spinning translating needle resulting from the translating, rotating movement of the device 100 of the present invention, causes the needle 210 to spiral in, rather than deflecting on a side, and so the needle ends out closer to the target. Such spinning translating needle movement also should break the static friction between the tissue and the target thereby reducing forces and further possibly reducing insertion forces.

The gripper mechanism of the Robot arm holds the needle by its head so it can support the needle from its head and provides an additional needle support guide, the gripper part which is located in close proximity of the skin entry point. This is similar to holding a needle with two hands, one from its head and one from its barrel next to the skin, where one hand pushes the needle in and out, and the lower holds the guide to support the direction of the needle as close as possible to the skin. This mechanism is configured to release the needle 210 quickly, automatically, and very smoothly, without moving or pushing on the needle.

The distance sensor and the force sensor measure the interaction force of the needle insertion with the patient and the force of needle. Alternatively, the interaction of the needle with the skin entry point can be measured. Distance sensor further are used in the present invention to calculate the distance of the needle with the target.

The mechanism of the present invention overcome the previous systems which is no information available to determine the direction of the needle during insertion. Also, no proper imagers are available to follow it in real time and the images are not real time. Since the gripper grips and controls the needle, it can control the direction of the needle and measures the interaction of the needle with the tissues, this can be utilized to provide real-time information regarding the direction of needle deflection, which in turn can be used as a feedback for corrections by accordingly positioning and orienting the needle.

The operation of the device 100 in combination with other components including the robotic arm 200, the MRI 500 and the helmet 400 is achieved by a control system. The controller is any of a number of devices known to those skilled in the art which can control the functionalities of the device and carry out the commands and signal processing necessary to control the functionalities, monitor input parameters and provide outputs. The controller includes a microprocessor, memory, storage memory for storing programs or applications used to carry out the functions of the controller. The device may include a display unit to display information responsive to signals outputted by the controller.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

With respect to the above description, it is to be realized that the optimum relationships for the parts of the invention in regard to size, shape, form, materials, function and manner of operation, assembly and use are deemed readily apparent and obvious to those skilled in the art, and all equivalent relationships to those illustrated in the drawings and described in the specification are intended to be encompassed by the present invention.

What is claimed is:

1. An electroacupuncture device for causing a needle to be inserted into an acupoint, said device comprising:
   a) a Magnetic resonance imaging (MRI);
   b) a Robotic arm movable in one or more dimension, comprising:
      i. a tip portion comprising an acupuncture needle having a distal end and a proximal end, and
      ii. a gripper mechanism coupled to the robotic arm, wherein the robotic arm is movable to position the needle smoothly in and out of the acupoint with respect to a target area; said gripper mechanism comprising:
         a set of gripper finger wherein the needle is gripped by the set of gripper finger and released, and a Gripper Long Pin; said Gripper long pin comprising a threaded distal end to connect with a solenoid pin to drive the set of gripper fingers; said solenoid operably coupled to the gripper mechanism to drive the gripper long pin along a linear trajectory;
         wherein the gripper mechanism holds the needle from the distal end and the proximal end in close proximity of the acupoint to guide the direction of the needle as close as possible to the acupoint and release the needle quickly, automatically, and smoothly, without moving or pushing on the needle;
   c) a linear and rotational mechanism operably coupled to the tip portion comprising: a linear motor configured to cause the gripper long pin to move along an axis and a rotational structure configured to cause the gripper long pin to rotate about an axis, and wherein the needle exits when the set of gripper fingers are open, and the spinning translating needle causes the needle to spiral in, rather than deflecting on a side so that the needle ends out closer to the acupoint and break the static friction between the acupoint and the target thereby reducing forces and further possibly reducing insertion forces, and
   d) a control system to control the functionalities of the device,
whereby the device performs most of human acupuncture techniques with more efficiency and reduce human errors.

2. The electroacupuncture device of claim 1, wherein the Robotic arm is a 6-DOF Robotic arm.

3. The electroacupuncture device of claim 1, wherein the device has an acupuncture MRI helmet for the treatment of traumatic brain injury and cerebral thrombosis.

4. The electroacupuncture device of claim 1, wherein the needle further has a vibration motor to cause the vibration of the needle.

5. The electroacupuncture device of claim 1, further provides a heating and cooling mechanism installed on the gripper for heating or cooling the needle.

6. The electroacupuncture device of claim 1, wherein the helmet has an airbag to be inflated and deflated to be fit on a head of a patient and a coil for MRI imaging to show most of the acupoints.

7. The electroacupuncture device of claim 1, further has a ultrasonic distance sensor with a measurement range of 1 cm-400 cm for determining the distance of the needle from the target point.

8. The electroacupuncture device of claim 1, further has a force sensor to control and measure the needle inserting force.

* * * * *